United States Patent
Cohn et al.

(10) Patent No.: US 9,469,533 B2
(45) Date of Patent: Oct. 18, 2016

(54) RENEWABLE ELECTRICITY CONVERSION OF LIQUID FUELS FROM HYDROCARBON FEEDSTOCKS

(71) Applicant: INENTEC INC., Richland, WA (US)

(72) Inventors: Daniel R. Cohn, Cambridge, MA (US); Jeffrey E. Surma, Richland, WA (US); Leslie Bromberg, Sharon, MA (US)

(73) Assignee: INENTEC INC., Bend, OR (US)

( * ) Notice: Subject to any disclaimer, the term of this patent is extended or adjusted under 35 U.S.C. 154(b) by 386 days.

(21) Appl. No.: 14/077,094

(22) Filed: Nov. 11, 2013

(65) Prior Publication Data

US 2014/0100294 A1 Apr. 10, 2014

Related U.S. Application Data

(63) Continuation of application No. 12/575,305, filed on Oct. 7, 2009, now Pat. No. 8,614,364, which is a continuation-in-part of application No. 11/177,152, filed on Jul. 6, 2005, now abandoned.

(60) Provisional application No. 61/107,563, filed on Oct. 22, 2008, provisional application No. 61/103,397, filed on Oct. 7, 2008.

(51) Int. Cl.
*C07C 1/00* (2006.01)
*C01B 3/36* (2006.01)
(Continued)

(52) U.S. Cl.
CPC . *C01B 3/36* (2013.01); *C01B 3/24* (2013.01); *C07C 29/15* (2013.01); *C10G 2/00* (2013.01); *C10G 2/32* (2013.01); *C10J 3/00* (2013.01); *F23G 5/46* (2013.01); *C01B 2203/0272* (2013.01); *C01B 2203/085* (2013.01); *C01B 2203/0833* (2013.01); *C01B 2203/0861* (2013.01); *C01B 2203/0866* (2013.01); *C01B 2203/1241* (2013.01); *C01B 2203/84* (2013.01); *C01B 2203/86* (2013.01); *C10G 2400/02* (2013.01); *C10G 2400/04* (2013.01); *C10G 2400/08* (2013.01); *C10J 2300/093* (2013.01); *C10J 2300/0916* (2013.01); *C10J 2300/0946* (2013.01); *C10J 2300/0959* (2013.01); *C10J 2300/1284* (2013.01); *C10J 2300/1659* (2013.01); *C10J 2300/1684* (2013.01); *C10J 2300/1846* (2013.01); *F23G 2206/203* (2013.01); *Y02E 20/12* (2013.01); *Y02E 50/13* (2013.01); *Y02E 50/32* (2013.01); *Y02P 20/133* (2015.11); *Y02P 20/134* (2015.11); *Y02P 20/145* (2015.11); *Y02P 20/582* (2015.11); *Y02P 30/10* (2015.11); *Y02P 30/30* (2015.11)

(58) Field of Classification Search
CPC ............ C10G 1/00; B09B 3/00; F23G 5/006
USPC .......................................................... 585/240
See application file for complete search history.

(56) References Cited

U.S. PATENT DOCUMENTS

| | | |
|---|---|---|
| 4,341,069 A | 7/1982 | Bell et al. |
| 5,713,195 A | 2/1998 | Bronicki et al. |

(Continued)

*Primary Examiner* — Nina Bhat
(74) *Attorney, Agent, or Firm* — Dorsey & Whitney LLP

(57) ABSTRACT

A method for converting renewable energy source-electricity and a hydrocarbon feedstock into a liquid fuel by providing a source of renewable-electrical energy in communication with a synthesis gas generation unit and an air separation-unit. Oxygen from the air separation unit and a hydrocarbon feedstock is provided to the-synthesis gas generation unit, thereby causing partial oxidation reactions in the synthesis gas-generation unit in a process that converts the hydrocarbon feedstock into synthesis gas. The synthesis gas is then converted into a liquid fuel.

29 Claims, 8 Drawing Sheets

(51) Int. Cl.
*C01B 3/24* (2006.01)
*C10G 2/00* (2006.01)
*C10J 3/00* (2006.01)
*F23G 5/46* (2006.01)
*C07C 29/15* (2006.01)

(56) References Cited

U.S. PATENT DOCUMENTS

| | | |
|---|---|---|
| 5,955,039 A | 9/1999 | Dowdy |
| 6,187,465 B1 | 2/2001 | Galloway |
| 6,630,113 B1 | 10/2003 | Surma |
| 6,669,744 B2 * | 12/2003 | Allam ............... F25J 3/04612 48/127.9 |
| 6,686,556 B2 * | 2/2004 | Mitchell ............... B09B 3/00 110/233 |
| 6,737,604 B2 * | 5/2004 | Surma ............... F23G 5/006 110/346 |
| 7,989,507 B2 | 8/2011 | Rising |
| 2004/0251241 A1 | 12/2004 | Blutke et al. |
| 2006/0096298 A1 | 5/2006 | Barnicki et al. |
| 2006/0130402 A1 * | 6/2006 | Wheat ............... B01D 53/047 48/197 R |
| 2007/0017228 A1 | 1/2007 | Surma |
| 2007/0017864 A1 | 1/2007 | Price et al. |

\* cited by examiner (a)

(b)

RENEWABLE ELECTRICITY CONVERSION OF LIQUID FUELS FROM HYDROCARBON FEEDSTOCKS

CROSS REFERENCE TO RELATED APPLICATIONS

This application is a continuation of U.S. patent application Ser. No. 12/575,305, filed on Oct. 7, 2009, issued as U.S. Pat. No. 8,614,36 on Dec. 24, 2013, which is a continuation-in-part of U.S. patent application Ser. No. 11/177,152, filed Jul. 6, 2005, now abandoned, which further claims priority to U.S. Provisional Application No. 61/103,397, filed Oct. 7, 2008, and U.S. Provisional Application No. 61/107,563, filed Oct. 22, 2008. These applications are incorporated herein by this reference in their entirety and for any purpose.

TECHNICAL FIELD

This invention relates to a system for optimal use of variable electricity from a renewable energy source, such as from wind and solar, in the production of liquid fuels from various hydrocarbon feedstocks, and/or from water and from $CO_2$. The hydrocarbon-based feedstocks include municipal and industrial waste, biomass, coal and natural gas. The liquids fuels that are produced include methanol, synthetic diesel and ethanol.

In one aspect of the invention, the renewable energy source electricity powers an oxygen separation unit which provides oxygen for partial oxidation conversion into synthesis gas. The synthesis gas may then be converted into liquid fuels. The renewable energy source electricity is also employed to power plasma and melter technologies which are used to enhance the conversion process. The system provides means to maintain liquid fuel production at a desired level by use of supplemental electricity from non-renewable sources and from storage of the oxygen In addition it provides the flexibility to operate at substantially reduced liquid fuel production levels. The cost of electricity used in the hydrocarbon to liquid fuel conversion facility is reduced by colocating the facility at a wind or solar energy farm. In addition, the electricity cost is minimized by using surplus wind or solar electricity that cannot be accommodated by a downstream load or by the electrical transmission system. Embodiments that involve electrolytic and pyrolytic production of hydrogen are also described. In addition, landfill gas can be used to provide power for the hydrocarbon to liquid fuel production process.

BACKGROUND OF THE INVENTION

Wind and solar power can provide important new sources of electricity that are renewable and do not contribute to greenhouse gas generation. However, these sources provide the electricity in a highly variable manner. This makes it difficult to match the electricity production to the needs of the electrical utilities that consume it. In addition, the electrical transmission system capability will need to be increased in order to move the electricity from where it is generated to where it is consumed. A further issue is that electricity does not provide a means to make a substantial reduction in petroleum use in the near term since it cannot be used to directly replace petroleum use in present cars and trucks. A major switch to plug in hybrids and electric vehicles would be required.

Various forms of storage of renewable electricity have been proposed to deal with the variability of production. They include pumped water and compressed air. However, these approaches have substantial cost and scale issues, and are limited in location. Another approach that has been suggested is to use the electricity to manufacture hydrogen as discussed below. None of these approaches provide easily substituted fuels for petroleum based transportation fuels.

There is a substantial literature on concepts for the use of electricity from renewable sources for the generation of hydrogen including [M. Hsu, Renewable Energy operated Hydrogen Reforming System, International Patent WO 2004/071947; Levene, J. I., M. K. Mann, R. Margolis, and A. Milbrandt, An Analysis of Hydrogen Production from Renewable Electricity Sources, National Renewable Energy Laboratory, Presented at ISES 2005 Solar World Congress, Orlando, Fla., Aug. 6-12, 2005, NREL/CP-560-37612 (2005); Bartholomy, O., Renewable Hydrogen From Wind In California, Proceedings, National Hydrogen Association, March 2005.

Some of these processes are electrolysis based. However, the purpose of these concepts is for a hydrogen-based economy. There are problems with distribution, storage, use of hydrogen that in most cases are not acknowledged by the authors, and the common usage of electrolysis releases the oxygen generated in the process rather than utilizing it in a beneficial way.

Use of renewable electricity to produce liquid fuels for transportation can provide a means to both address the issue of the variability from wind and solar energy and also convert it into an energy form which has greatest near term impact for reducing use of petroleum. The problem of the highly variable nature of electricity generation can be more easily addressed when the electricity is used in this manufacturing application rather than when it has to be matched to the needs of the electrical grid.

Plasma technology offers a way for using electricity for conversion of natural gas and other hydrocarbon fuels into synthesis gas (syngas). Synthesis gas can then be used to make a variety of fuels. Conventional thermal plasmas have been used. [CORMIER, J. M., RUSU I., Syngas production via methane steam reforming with oxygen: plasma reactors versus chemical reactors: The future of technological plasmas, Journal of physics. D, Applied physics vol. 34, no18, pp. 2798-2803 (2001); see also Chun, Y. N., Kim, S. C., Production of hydrogen-rich gas from methane by thermal plasma reform, Journal of the Air and Waste Management Association, v 57, n 12, December, 2007, p 1447-1451]. Also, nonthermal plasma have been used [Nozaki, T., Tsukijihara, H., Fukui, W., Okazaki, K., Kinetic analysis of the catalyst and nonthermal plasma hybrid reaction for methane steam reforming, Energy and Fuels, v 21, n 5, September/October, 2007, p 2525-2530; also, Ouni, F., Khacef, A. Cormier, J. M., Effect of oxygen on methane steam reforming in a sliding discharge reactor, Chemical Engineering and Technology, v 29, n 5, May, 2006, p 604-609]. Microwave discharges have also been suggested [Jasinski, M., Dors, M., Mizeraczyk, J., Production of hydrogen via methane reforming using atmospheric pressure microwave plasma, Journal of Power Sources, v 181, n 1, Jun. 15, 2008, p 41-45] The present invention overcomes these drawbacks of these approaches.

SUMMARY OF THE INVENTION

The present invention includes a method for converting renewable energy source electricity and a hydrocarbon feedstock into a liquid fuel. One aspect of the present invention operates by providing a source of renewable electrical energy in communication with a synthesis gas generation unit. An air separation unit IS also provided in communication with the synthesis gas generation unit. Electricity from the source of renewable electrical energy is then used to power the air separation unit. As is common with renewable energy sources, the electrical energy will typically vary over time. Oxygen from the air separation unit and a hydrocarbon feedstock is also provided to the synthesis gas generation unit, thereby causing partial oxidation reactions in the synthesis gas generation unit in a process that converts the hydrocarbon feedstock into synthesis gas. The synthesis gas is then converted into a liquid fuel. In this manner, it is possible to adjust the liquid fuel production level to a desired level when the amount of renewable source electricity is reduced. While not meant to be limiting, the source of renewable energy may be wind power or solar power.

This embodiment of the present invention finds particularly advantages when the hydrocarbon feedstock is provided as municipal waste. Another aspect of the present invention is found when a variable amount of electricity from a second electrical source is provided to maintain the liquid fuel production at a desired level. While not meant to be limiting, it is preferred that the second electricity source is an engine generator, a gas turbine, a fuel cell, and combinations thereof. Also while not meant to be limiting, the second electricity source is fueled with a hydrocarbon fuel, such as natural gas.

Another aspect of the present invention that provides particular advantages is when the source of renewable electrical energy, the synthesis gas generation unit, the air separation unit, and the second electricity source are co-located. In such applications, particular advantage is found when DC current is used to transmit power from the renewable energy electricity source to the synthesis gas generation unit.

The electricity from the renewable energy source may be used to power a plasma included in the synthesis gas generation unit, a joule heated melter included in the synthesis gas generation unit, or combinations thereof. At least a portion of the oxygen produced by the air separation unit may also be stored for use at a later time. While not meant to be limiting, the air separation unit is preferably provided as a cryogenic separation unit. Also while not meant to be limiting, the oxygen produced in the air separation unit is preferably stored cryogenically. Another advantage of the present invention is the capability to vary the relative amounts of plasma heating, melter heating, oxygen and steam provided in the synthesis gas generation unit in response to variations in the amount of renewable energy source electricity. While not meant to be limiting, it is preferred that the electricity to the joule heated melter included in the synthesis gas generation unit is reduced at disproportionately smaller amount when the electricity input from the renewable energy source to the synthesis gas generation unit is reduced. The present invention may also include embodiments where at least some of the electricity from the renewable energy source is provided to a transmission system for use by a downstream user.

Another embodiment of the present invention replaces the air separation unit with an electrolysis unit. In an embodiment that includes and electrolysis unit, at least a portion of the oxygen produced in the electrolysis unit may be saved for use at a later time, and oxygen produced in the electrolysis unit may stored cryogenically. When utilizing an electrolysis unit, the present invention may produce liquid fuel by reacting $CO_2$ generated from the hydrocarbon feedstock with hydrogen produced in the electrolysis unit. In this type of arrangement, some of the renewable energy source electricity may be used for compressing $CO_2$.

BRIEF DESCRIPTION OF THE DRAWINGS

The following detailed description of the embodiments of the invention will be more readily understood when taken in conjunction with the following drawings, wherein.

DETAILED DESCRIPTION OF THE PREFERRED EMBODIMENTS

Figure 1:
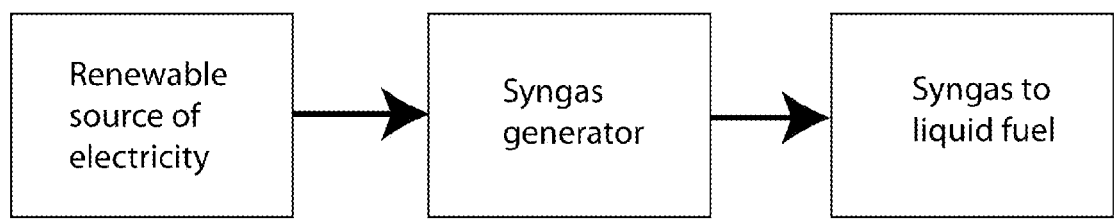
FIG. 1 is a schematic diagram of hydrocarbon feedstock to liquid fuel conversion system using renewable energy electricity.

For the purposes of promoting an understanding of the principles of the invention, reference will now be made to the embodiments illustrated in the drawings and specific language will be used to describe the same. It will nevertheless be understood that no limitations of the inventive scope is thereby intended, as the scope of this invention should be evaluated with reference to the claims appended hereto. Alterations and further modifications in the illustrated devices, and such further applications of the principles of the invention as illustrated herein are contemplated as would normally occur to one skilled in the art to which the invention relates.

It is the purpose of this invention to provide systems for improved use of electricity from renewable energy sources, such as wind or solar energy, through the conversion of hydrocarbon feedstocks into a liquid fuel. The feedstocks include municipal and industrial waste, biomass, coal and natural gas. These systems can both reduce the cost of producing liquid fuels from hydrocarbon feedstocks and also decrease $CO_2$ emissions.

The liquid fuels that can be produced include, but are not limited to, methanol (either as a fuel itself or as a feedstock for making DME or gasoline), ethanol, synthetic diesel (Fischer-Tropsch), aviation fuel, and combinations thereof.

Use of renewable energy sources can play an important role because of the relatively large amount of electricity that is used in present processes that convert hydrocarbon feedstocks into liquid fuels. The electrical energy can be 10% to 15% of the chemical energy in the liquid fuel that is produced and the hydrocarbon chemical energy needed to produce this electricity can thus approach 50% of the chemical energy of the liquid fuel. The primary use of the electricity is generally for providing oxygen from air separation for partial oxidation conversion of these feedstocks into synthesis gas which is then converted into liquid fuels. It may also be used for various forms of electrical heating, including plasma heating and resistive heating of molten material, that enhance the conversion process.

This invention involves systems which use renewable energy sources in an optimal way to reduce the cost of electricity for production of liquid fuels from hydrocarbon feedstocks. The use of renewable electricity also reduces the amount of greenhouse gas that is generated in the production of these fuels. The renewable energy source electricity is employed in ways to achieve the greatest cost and $CO_2$ reductions. The systems accommodate the variable nature of the renewable electricity by optimal use of additional electricity sources, and oxygen storage. They also involve hydrocarbon feedstock to synthesis conversion systems that have high turn down ratios (the ratio of maximum syngas production to minimum allowed production).

The system is shown in FIG. 1. The electricity is employed to provide the power for conversion of a hydrocarbon feedstock. The conversion process produces a synthesis gas (syngas), which is a mixture of hydrogen and carbon monoxide. A preferred conversion process uses partial oxidation with oxygen produced by separation unit which is partially or completely powered by the electricity from wind or solar energy. The syngas is then converted by catalytic means into liquid fuels as shown in FIG. 1.

Figure 2:
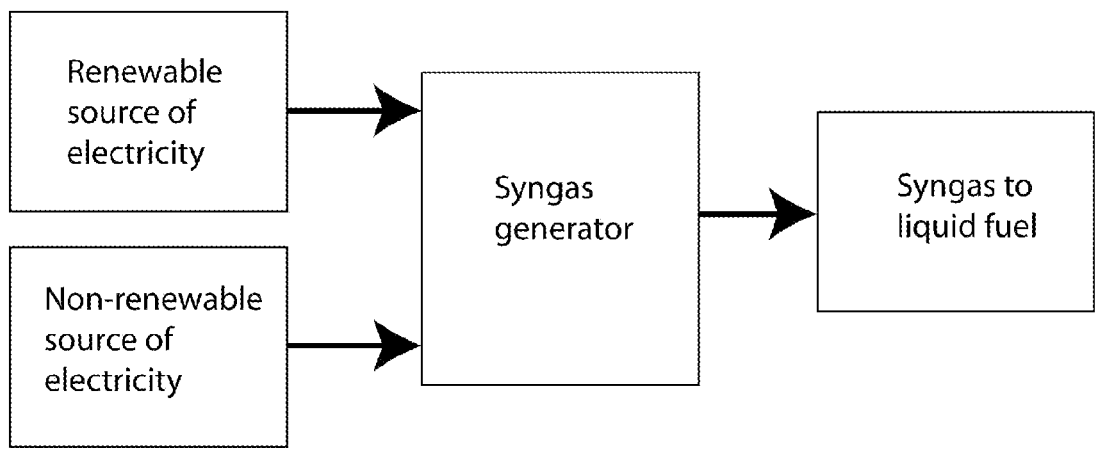
FIG. 2 is a schematic diagram of hydrocarbon feedstock to liquid fuel conversion system using variable electricity from non-renewable source (such as natural gas) to augment or replace renewable energy electricity.

When the level of renewable electricity is reduced, because of the variable nature of the source, the liquid fuel production plant can be run at a lower production level. Alternatively or in addition, replacement electricity from an onsite non-renewable gas powered source could be used to achieve a desired level of plant operation as shown in FIG. 2. The non-renewable gas could include natural gas and syngas from either air blown or oxygen blown partial oxidation systems which use various feedstocks. The electricity could be provided by an engine-generator set, a gas turbine or a fuel cell. Another option, if all that is needed to replace the renewable energy source electricity is heat, is to use combustion of non-renewable feedstocks to provide the energy required for the process. In addition, as described below stored oxygen can also be used as a means to maintain the desired level of liquid fuel production plant operation.

It is preferred that the liquid fuel production plant can be co-located at the wind turbine or solar energy site. In this way the cost of transmitting the electricity is greatly reduced. There is also advantage of co-location in that the preferred manner to distributed the electricity from the renewable to the syngas generator is through DC. Distributed electricity generation benefits from DC harnessing of the electricity because AC generation can from multiple units is more difficult to synchronize (from multiple wind turbines, for example), or generated DC, as is the case with photovoltaics. There is limited DC transmission, and thus it would be best if the syngas generator is close to the renewable energy source.

Thus there are a range of possibilities for using the supplemental nonrenewable energy source. The non-renewable energy could be used as a heat (i.e., combustion) in addition to, or instead of, generating the electricity to be used in the process. The electricity could be used as the source of energy for the process (for example as source of power for plasma heating) as well as for oxygen production. It could also be used for gas compression or gathering the $CO_2$ to be converted into methanol by reaction with hydrogen (from the atmosphere, separated from flue gases, etc.).

Figure 3:
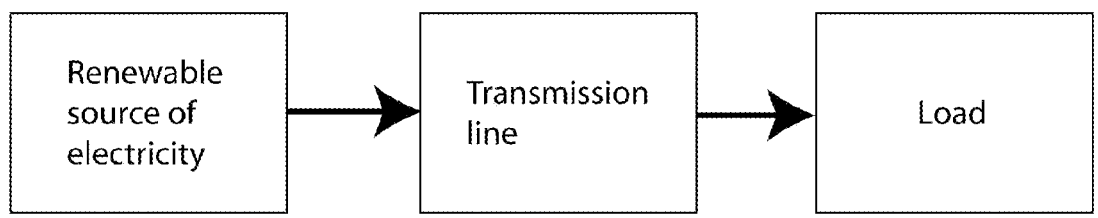
FIG. 3 is a schematic diagram of an electrical system for use of surplus renewable electricity.
Figure 3:
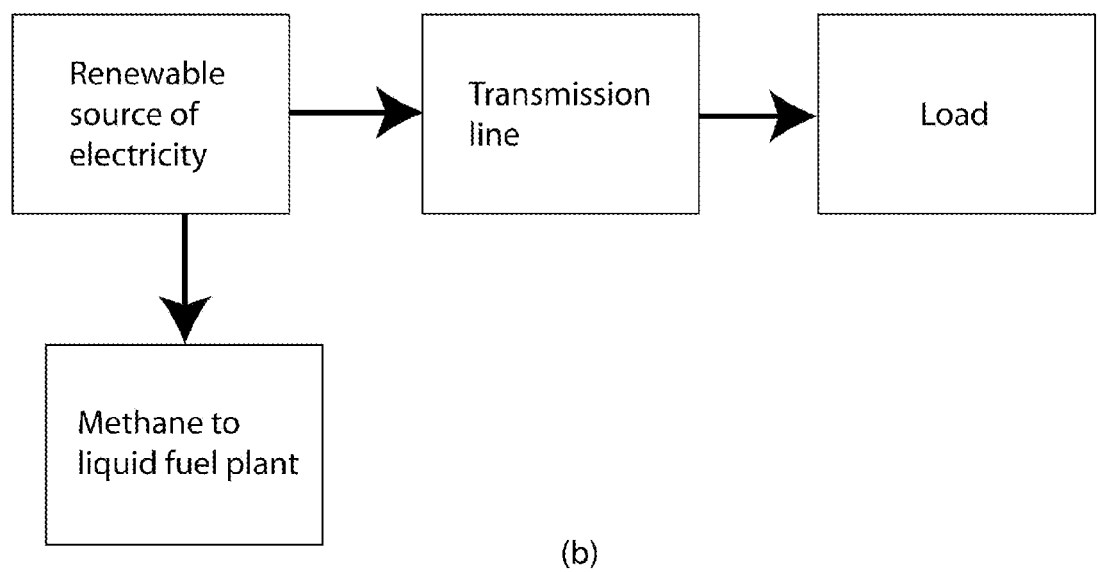

In one embodiment of the invention, some or all of the electricity from the renewable energy source is fed at some point in time into the electrical grid for use in a downstream load. A schematic diagram of the overall electrical system is shown in FIG. 3. FIG. 3a shows conditions where all the electricity generated by the renewable energy farm is consumed by the downstream power load. All the electricity generated is fed to the transmission line. In the case of FIG. 3b, not all the power that can be generated by the renewable electricity farm is needed by the downstream electrical load or can be accommodated by the electrical transmission system and thus there is extra power that cannot be fed to the transmission line. In this case, the surplus electricity is used to drive the conversion of the hydrocarbon feedstock such as natural gas (which is mainly methane) to syngas followed by conversion of synthesis gas to a liquid fuel. The conversion of natural gas could be accomplished by endothermic plasma reforming.

Figure 4:
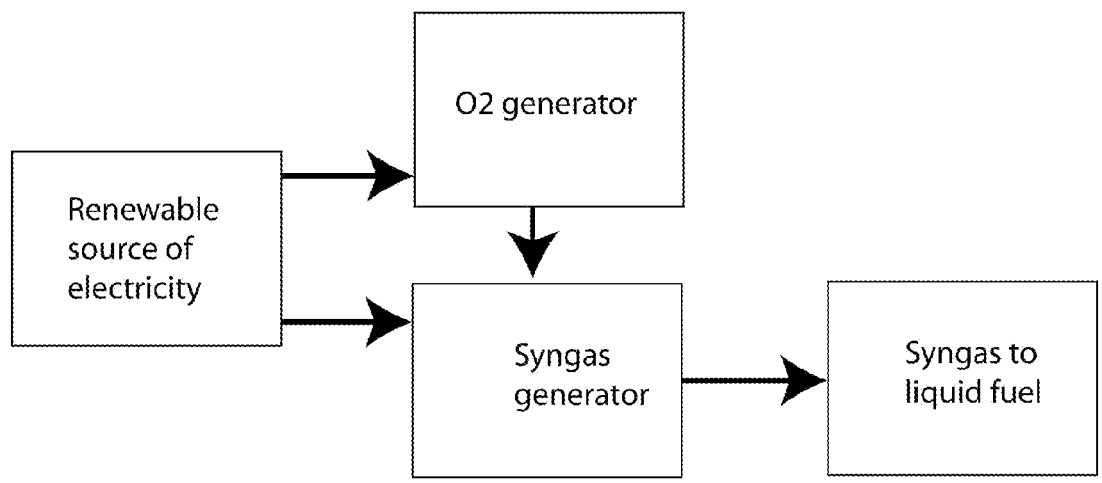
FIG. 4 is a schematic diagram showing the use of renewable electricity for oxygen production for real time use in partial oxidation conversion of hydrocarbon feedstocks or for storage.

The electricity from the renewable energy sources could also be used to power an oxygen separation plant which provides oxygen for partial oxidation based conversion of natural gas or another hydrocarbon feedstock into synthesis gas. The use of surplus electricity to power an oxygen separation unit could be in addition to or instead of it's in powering a heat source for the process, as shown in FIG. 4. The electricity-driven heat source for the process could be a resistive heater in the process, a plasma or an induction heater.

Both endothermic and exothermic plasma based reforming can be used. The advantage of endothermic plasma reforming is that there is no loss of energy as is the case in partial oxidation (which is an exothermic reaction). In the case of steam reforming of natural gas, plasma reforming avoids the need of consuming some of the natural gas to drive the endothermic process. The energy required by the endothermic reaction is the surplus power from the renewable source. Operation close to autothermal reforming which uses partial oxidation combined with steam reforming or $CO_2$ reforming could increase the throughput of the methanol generation and allows flexibility of production of the liquid fuel. The plasma energy increases the energy content of the synthesis gas.

Several options for conversion of hydrocarbon feedstocks to synthesis gas are available partial oxidation, steam reforming, $CO_2$ reforming, pyrolysis or a combination of the four. The first case is exothermic, with high temperatures, while steam reforming and $CO_2$ reforming are endothermic. Pyrolysis is also endothermic, although to a lower degree than $CO_2$ or steam reforming. A combination of several of these operations would result in optimal synthesis gas for the methanol production, which calls ideally for a ratio of $H_2$ to CO of 2, for the reaction

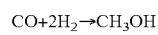

In general, the reforming equation for natural gas that generates this ratio of $H_2$ to CO can be written as:

where natural gas is represented by methane.

An additional constraint is that A, B, C, and D need to be positive (i.e., no removal of a compound). It can be easily shown that $B = 1 - A$ $C = 2 - 2A$ $D = \frac{1}{2}(1 - 2B - C) = \frac{1}{2}(-3 + 4A)$ For B, C, D>0, it is required that $1 > A > \frac{3}{4}$ Although the above example is for methanol production, there are other means of optimization of the feedstock for ethanol, or for ethanol/methanol blends, and for heavier alcohols, such as butanol. However, methanol is by far the easiest one to produce, with high selectivity and efficiency, while ethanol is substantially less selective (ethanol/methanol mixtures are generated in this case).

Figure 5:
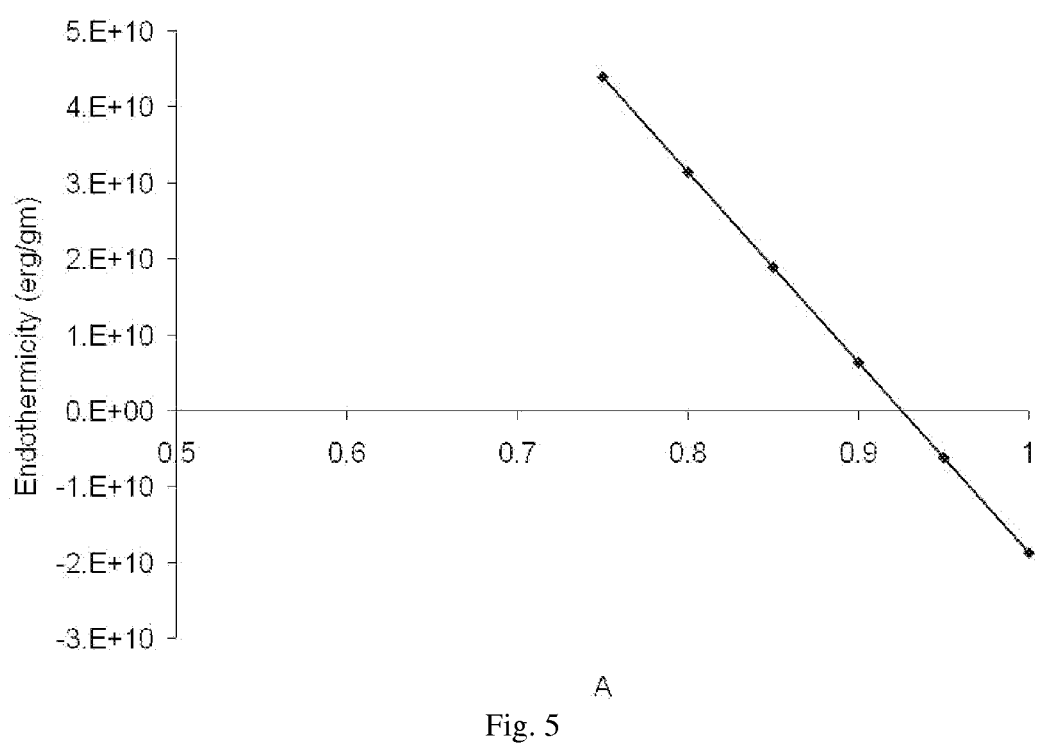
FIG. 5 is a graph showing the dependence of endothermicity on parameter A.

There is a range of $O_2$ addition that allows the reaction endothermicity to be varied (most endothermic for $A = \frac{3}{4}$, that is, without the addition of free oxygen, to most exothermic for $A = 1$, corresponding to partial oxidation), allowing the adjustment of the flow rate of synthesis gas for a given power from the renewable source. The endothermicity as a function of the parameter A in the above equations is shown in FIG. 5. At A>0.93, the reaction is exothermic, and heat is released. FIG. 5 is calculated assuming thermal equilibrium at 25 bar and 1300 K, conditions appropriate for generation of syngas from methane.

Methane conversion is high at these conditions. Whatever methane is left can be recycled before the catalyst which is used to convert the syngas to liquids, or after the catalyst, where simple condensation of the liquid fuel allows for the separation of the unconverted methane.

Figure 6:
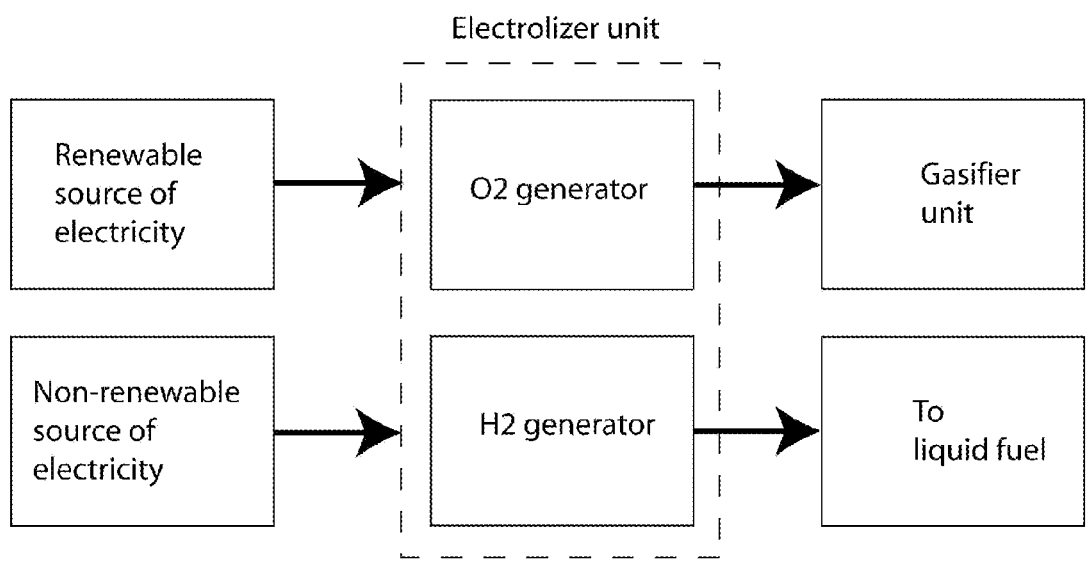
FIG. 6 is a schematic diagram showing the use of renewable or non-renewable energy for electrolytical manufacturing of $H_2$ and $O_2$

It is also possible to use electrolysis to generate both the hydrogen and oxygen required for all or some of the process, as shown in FIG. 6. The oxygen generated in the electrolysis process could be used in the syngas generator or in other plants, also collocated, that use it to generate syngas from various sources, including biomass and coal. Thus not only is the hydrogen generated by the electrolysis useful, but so is the oxygen, and it is not released to the atmosphere. The hydrogen can be reacted with $CO_2$ from the gasification unit to produce liquid fuel and reduce $CO_2$ emissions.

The possibility of using electrolyzers to augment the hydrogen in the system, or to provide all the hydrogen required, is attractive. The advantage of electrolyzer-based hydrogen generators is that they have large turn down ratios. The turn down ratio is much larger than that of other large hydrogen production devices. The hydrogen and/or oxygen could be stored during times where the production exceeds the generating capability of the liquid fuel production plant, or the plant could be designed to manage the maximum hydrogen production. Similarly, the oxygen can be used or stored in a gasification plant next to the electrolyzer units.

Turn down ratios of power as high as 2 have been determined for catalyzed partial oxidation (CPO) [Dave, N. and G. A. Foulds, Comparative Assessment of Catalytic Partial Oxidation and Steam Reforming for the Production of Methanol from Natural Gas, Ind. Eng. Chem. Res. 34, 1037-1043 1037 (1995)]. It should be noted that for the application of the present invention, the advantage is not necessarily just the minimization of the electrical power requirement, as it is needed to use some of it in order to increase the heating value of the methanol and thus use it to "store" the electrical energy provided by the renewable electricity generator. This is the case both for the synfuel generator as well as the methanol or liquid fuel stages in the process.

Large plants that minimize the cost of manufacturing and the efficiency of conversion use large scale, with limited turn down ratio, as the space velocity of the compounds needs to be constant. These large plants use single train to obtain advantages of scale. In order to provide the required turn down ratio, it is necessary to operate the liquid fuel out-of-optimal range. Thus, the use of energy from both the renewable source as well as the one non-renewable source to maintain the optimal performance of the liquid fuel plant results in improved performance. However, during times of off-optimal performance, the throughput of the plant should be varied. By using an inexpensive source of energy for most of the process, the increased relative cost of the methanol produced during non-optimal times does not affect the overall economics of the plant.

There are other ways to maintain constant productivity of the plant. For example, the rate of production of synthesis gas for optimal generation of methanol can be adjusted, for a given power, by adjusting the concentration parameters indicated about (varying A). Alternatively, the rate of synthesis gas generation can be adjusted by varying the electrical power provided by the renewable energy source, at constant concentration parameters.

By using an electricity-driven reformer, and in particular, plasma driven reformers, it is possible to stabilize the synthesis gas generating unit. Conventional synthesis units have very narrow operating parameters. In a preferred embodiment, the electricity is introduced into the reaction chamber by a plasma discharge. The use of electrically heated molten material in conjunction with a partial oxidation process can also be used to stabilize operation and provide a high turn down ratio. The molten material can be kept hot with a small amount of electricity and can be a very effective way to run the system at idle. The molten material can be kept hot as the liquid fuel production rate is decreased by increasing the percentage of total electricity consumption that is used for joule or inductive heating of the melter.

For optimal plasma operation, the region of the electrodes can be protected by a sheath gas, especially in the case with substantial amounts of steam, This not only minimizes the erosion, it also minimizes the coking of the electrodes by the natural gas. In the case of substantial amounts of steam, the discharge results in very aggressive conditions that rapidly erode the electrodes. The plasma discharge could be AC or DC. However, DC is preferred for plasma stability. Also, DC fits better the power conditioning equipment, as most renewable power sources would generate DC either directly (as in the case of photovoltaics) or downstream, (as is the case of wind farms, if it is not possible to synch the AC power produced by the multiple windmills, thus the electricity from each windmill needs to be rectified before combining its power with the power from the other units in the wind farm).

The production and use of oxygen can be varied so as to optimize the overall system performance. The oxygen can either be consumed as it is produced or stored using cryogenic storage. Cryogenic separation is attractive, as it is much easier to store during periods of high surplus power, as compared with membrane separation, which requires much larger volume, even at high pressures. The stored oxygen could be used to provide a buffer in the methane to syngas part of the plant in order to provide continued operation when there is no surplus energy to drive the endothermic reaction. When there is reduced electrical power, the stoichiometry in the above chemical reaction is varied (relative amounts of oxygen and steam and/or $CO_2$ are changed), increasing the relative amount of oxygen to make up the lack of electrical power.

The oxygen produced from the renewable electricity could also be used in partial oxidation processes for conversion of hydrocarbon feedstocks to syngas that do not involve the use of plasma, or partially involve the use of a plasma.

Pyrolysis processes can be used for the manufacturing of hydrogen and other products. Plasma heating can be used, with substantial yields of $C_2$ compounds (including acetylene), especially when including quenching.

Figure 7:
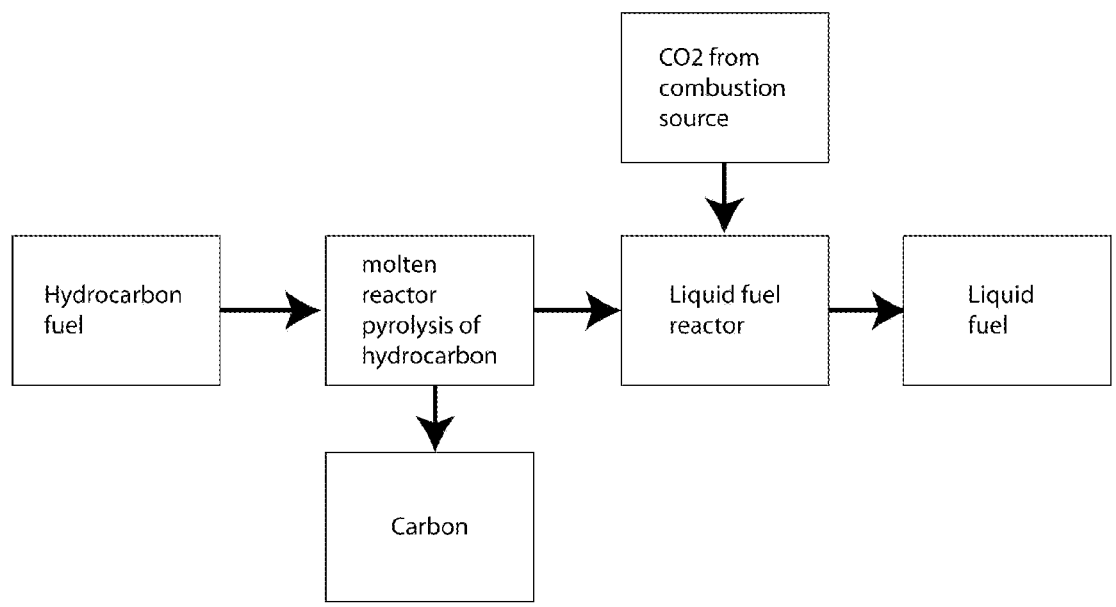
FIG. 7 is a schematic diagram showing a system for pyrolytic conversion of hydrocarbon feedstocks to liquid fuels. The system produces hydrogen by bubbling the hydrocarbon feedstock through a molten material. The hydrogen is then reacted with $CO_2$ to produce a liquid fuel.

In addition, a very attractive new alternative for using pyrolysis to produce a hydrogen-rich gas is to bubble methane or natural gas through a liquid material where the heat required form the pyrolytic process is supplied by plasma heating or by electrical resistance heating in the material as shown in FIG. 7. Use of molten glass is particularly attractive. Heat needs to be supplied to the molten material because the reaction is endothermic. The electrical heating can be supplied with electrodes submerged in a molten glass bath (Joule heating), through inductive heating using eddy currents, or a combination of the these methods each other or with plasma heating.

The pyrolysis reaction will separate the carbon from the methane resulting in gas that is mainly hydrogen. The hydrogen can then be reacted with $CO_2$ to form synthesis that is then used to produce various liquid fuels. The consumption of $CO_2$ can offset the generation of $CO_2$ which is released in when energy is extracted from the liquid fuel by combustion.

Methane pyrolysis in molten metals has been discussed previously [See, for example, Lewis, M. A. Serban, M., Marshall, C. L. and Lewis, D., Direct Contact Pyrolysis Of Methane Using Nuclear Reactor Heat, Argonne National Laboratory, 2001.] In contrast, this new approach would use electrical heating. Moreover, one embodiment would involve heating of a glass bath. Surplus electricity from the renewable energy source is used to provide the energy to the molten liquid required for the endothermic reaction. There are also potential advantages of using slags resulting from waste processing as the molten liquid that drives the pyrolysis, allowing the generation of carbon-based products in the slag.

Through this method it is possible to sequester the carbon from natural gas coal or another hydrocarbon fuel in a manner that is much more straight forward than is the case when the carbon is combusted which requires capture and sequestration of $CO_2$, a more challenging endeavor. The additional hydrogen is produced in this process that can shift the balance of oxygen, carbon and hydrogen to that which optimizes the production of the liquid fuels. This would allow the use in manufacturing of liquid fuels with high hydrogen content from feedstocks that are hydrogen poor. However, that the energy yield of the system is lower than then if the carbon is combusted.

A further feature of this process is that full conversion of the hydrocarbon fuel to hydrogen and carbon is not needed. The unconverted methane can be converted into synthesis gas in a downstream unit and the synthesis gas can then be converted into liquid fuels.

There are also potential methods for direct methanol generation through the use of nonthermal plasma discharges. [See, for example, Hijikata, K, Ogawa, K., Miyakawa, N., Methanol conversion from methane and water vapor by electric discharge (effect of electric discharge process on methane conversion), Heat Transfer Asian Research, 28, n 5, 1999, p 404-417]. In this case, either corona or dielectric barrier discharges are used to converted the mixture to methanol. Although this technique is substantially more power intensive than the direct conversion using high temperature, the advantage of this technique is very rapid response to the varying characteristics of the both the downstream use of the electricity or the varying generation of the power source (due for, for example, varying wind power).

The economics for these methods of employing renewable electricity to produce liquid fuels are attractive because the electricity cost is low. The cost of electricity could in fact be negative when the renewable energy source produces energy that exceeds what the electricity dispatcher asks for. Moreover, there is minimal electricity transmission system cost for the synthesis or hydrogen gas generation unit. While the most economically attractive approach is to use surplus renewable electricity that cannot be sent to the grid for downstream use, it is, also possible to use a greater fraction or all of the renewable generated electricity.

The system could be used to increase the use of stranded natural gas which cannot be transported to the end user by pipe line.

Another advantage of using renewable energy, such as windpower, is that the greenhouse gas emissions from converting natural gas into a liquid fuel are significantly reduced.

This approach for using excess renewable energy could also be employed in conjunction with electricity from geothermal energy. In addition, it could be applied to the utilization of unused heat in solar thermal plants prior to conversion to electricity. The heat could be used to provide the energy for a liquid used for the endothermic pyrolytic conversion of natural gas which is bubbled through it. A variation of this process is the use of both excess solar thermal energy and electricity from another source to heat the liquid.

When methane is mentioned as a hydrocarbon feedstock in the above discussion, it is meant to cover both natural gas or gas streams that contain substantial amounts of natural gas. Also included are tail gases from processing plants, producer gas, natural gas produced in oil drilling or landfill gas. In addition, it is possible to use solid or liquid hydrocarbons as the feedstock for the renewable energy electricity plasma reforming process, partial oxidation processes which use the electricity to power an oxygen separation unit, or a pyrolysis unit. These hydrocarbons include municipal and other forms of waste, coal, various forms of biomass and various forms of petroleum. In these applications natural gas generated electricity could be used to augment the electricity generated by wind or solar power.

Figure 8:
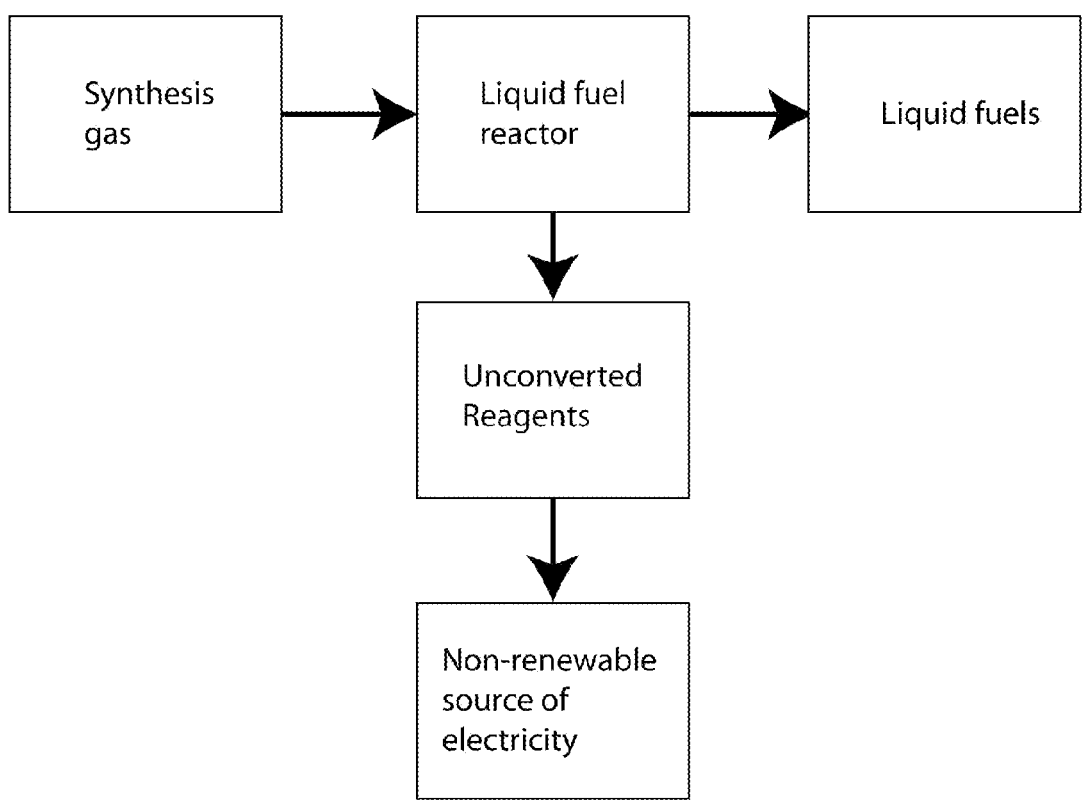
FIG. 8 is a schematic diagram showing a single pass reagents through a liquid fuel reactor, with unconverted reagents recycling to non-renewable source of electricity instead of recycle to liquid fuel reactor.

A complimentary approach is to use a single pass of the synthesis gas through the catalyst. Because conversion is not 100%, a substantial amount of the reagents are left unconverted. This is due to the fact that even at equilibrium there may be substantial amounts of unconverted reagents, or that the system does not reach equilibrium. In this case, the conventional technique is to separate the liquid fuels, and then recompress and recycle the unconverted reagents. An alternative approach is to use the unconverted reagents to drive the external electricity source, avoiding both the capital equipment and the power required for recompressing and recycling the unconverted flows. FIG. 8 shows a schematic diagram of the concept.

Landfill gas, which consists of methane and a relatively small amount of other hydrocarbon gases, may be a particularly attractive source of electricity production for waste to liquid fuels production facilities since existing landfills are preferred locations for these facilities. The landfill gas generated electricity can be used instead of wind and solar generated electricity in the applications described above. The landfill gas can be converted into electricity by an engine-generator set, a gas turbine or a fuel cell. The electricity can then be used to power an oxygen separation unit, plasma heating and/or a melter, or solar electricity generation. In addition to providing liquid fuels the landfill gas electricity powered system could also be used to produce hydrogen.

A combination of landfill gas generated electricity and wind or solar generated electricity could also be used to provide electricity for the liquid fuels from waste facility. The amount of landfill generated electricity could be varied so as to compensate for the variation in wind or solar generated electricity. The rate of gas extraction from the landfill can be controlled so as to compensate for the changes in wind or solar electricity generation. In order to minimize electricity transmission cost, the solar or wind electricity generation facility can be located at or adjacent to the landfill.

In a related application that does not involve a liquid fuels from waste facility, control of landfill gas extraction (or extraction of methane from other sources such as a natural gas production well or storage facility) for conversion into electricity can also be used to provide a desired level of electricity for sale from an electricity generation system that includes a variable electricity source such as wind or solar energy. The outputs of engine generator sets, gas turbines and fuel cells can be rapidly varied so as to employ landfill or other gas based electricity generation to compensate for changes in wind or solar powered electricity generation. In order to minimize electricity transmission cost, the solar or wind electricity generation facility can be located at or adjacent to the methane source.

In another embodiment the amount of landfill gas based electricity can be controlled when used in combination with electricity from the grid so as to minimize the overall electricity cost for the liquid fuel from waste conversion facility by using a larger relative amount of electricity from the grid at times when it is available at a lower price.

While the invention has been illustrated and described in detail in the drawings and foregoing description, the same is to be considered as illustrative and not restrictive in character. Only certain embodiments have been shown and described, and all changes, equivalents, and modifications that come within the spirit of the invention described herein are desired to be protected. Any experiments, experimental examples, or experimental results provided herein are intended to be illustrative of the present invention and should not be considered limiting or restrictive with regard to the invention scope. Further, any theory, mechanism of operation, proof, or finding stated herein is meant to further enhance understanding of the present invention and is not intended to limit the present invention in any way to such theory, mechanism of operation, proof, or finding.

Thus, the specifics of this description and the attached drawings should not be interpreted to limit the scope of this invention to the specifics thereof. Rather, the scope of this invention should be evaluated with reference to the claims appended hereto. In reading the claims it is intended that when words such as "a", "an", "at least one", and "at least a portion" are used there is no intention to limit the claims to only one item unless specifically stated to the contrary in the claims. Further, when the language "at least a portion" and/or "a portion" is used, the claims may include a portion and/or the entire items unless specifically stated to the contrary. Likewise, where the term "input" or "output" is used in connection with an electric device or fluid processing unit, it should be understood to comprehend singular or plural and one or more signal channels or fluid lines as appropriate in the context. Finally, all publications, patents, and patent applications cited in this specification are herein incorporated by reference to the extent not inconsistent with the present disclosure as if each were specifically and individually indicated to be incorporated by reference and set forth in its entirety herein.

The invention claimed is:

1. A method for converting hydrocarbon material to liquid fuel comprising:
utilizing electricity provided from a solar or wind powered renewable energy source to generate oxygen in one or more of an oxygen separation unit or an electrolysis unit;
supplying a combination of oxygen from at least the one or more of the oxygen separation unit or electrolysis unit and steam to a synthesis gas generation unit, wherein relative amounts of the oxygen and steam vary in accordance with an amount of the electricity provided from the solar or wind powered renewable energy source;
feeding hydrocarbon feedstock to the synthesis gas generation unit;
producing synthesis gas in the synthesis gas generation unit using a combination of steam reformation and partial oxidation of the hydrocarbon feedstock; and
converting the synthesis gas into a liquid fuel.

2. The method of claim 1, further comprising storing oxygen generated by one or more of the oxygen separation unit or electrolysis unit and using the oxygen at a later time.

3. The method of claim 1, wherein the oxygen separation unit or electrolysis unit is partially powered by the electricity from the solar or wind powered renewable energy source.

4. The method of claim 1, further comprising providing electricity from the solar or wind powered renewable energy source to power one or more plasma electrodes included in the synthesis gas generation unit.

5. The method of claim 4, wherein the amount of oxygen supplied varies in accordance with an amount of plasma produced in the synthesis gas generation unit.

6. The method of claim 1, further comprising generating oxygen in parallel with steam reformation of the hydrocarbon feedstock.

7. The method of claim 1, wherein the one or more of an oxygen separation unit or an electrolysis unit is an air separation unit.

8. The method of claim 1, wherein the one or more of an oxygen separation unit or an electrolysis unit is an electrolysis unit.

9. The method of claim 1, further comprising producing synthesis gas in the synthesis gas generation unit using endothermic plasma reforming.

10. The method of claim 1, further comprising using a combination of steam reformation and partial oxidation of the hydrocarbon feedstock to produce the synthesis gas.

11. The method of claim 10, wherein a ratio between steam reformation and partial oxidation used is based, at least in part, on energy available from other processes.

12. The method of claim 10, wherein the combination of steam reformation and partial oxidation achieves autothermal reforming.

13. The method of claim 10, wherein energy required to perform steam reformation is supplied by surplus electricity from the solar or wind powered renewable energy source.

14. The method of claim 10, wherein at least some energy released from the partial oxidation of the hydrocarbon feedstock is used to perform the steam reformation.

15. A system for converting hydrocarbon material to liquid fuel, the system comprising:
- at least one solar or wind powered renewable energy source configured to provide electricity;
- a synthesis gas generation unit operably coupled to the at least one solar or wind powered renewable energy source and configured to receive a combination of oxygen and steam, wherein relative amounts of the oxygen and steam vary in accordance with an amount of electricity from the at least one solar or wind powered renewable energy source, and wherein the synthesis gas generation unit is configured to produce synthesis gas using a combination of steam reformation and partial oxidation of the hydrocarbon feedstock; and
- a liquid fuel production plant configured to convert the synthesis gas into liquid fuel.

16. The system of claim 15, further comprising an oxygen producing unit configured to supply oxygen to the synthesis gas generation unit.

17. The system of claim 16, wherein the oxygen producing unit is configured to store oxygen produced and supply the oxygen at a later time.

18. The system of claim 16, wherein the oxygen producing unit is at least partially powered by the electricity from the at least one solar or wind powered renewable energy source.

19. The system of claim 16, wherein the synthesis gas generation unit comprises at least one plasma electrode powered by electricity provided from the at least one solar or wind powered renewable energy source.

20. The system of claim 19, wherein the oxygen producing unit is configured to vary an amount of oxygen supplied in accordance with an amount of plasma generated in the synthesis gas generation unit.

21. The system of claim 16, wherein the oxygen producing unit is configured to supply oxygen to the synthesis gas generation unit while the synthesis gas generation unit produces synthesis gas by steam reformation.

22. The system of claim 16, wherein the oxygen producing unit is an air separation unit.

23. The system of claim 16, wherein the oxygen producing unit is an electrolysis unit.

24. The system of claim 15, wherein the synthesis gas generation unit is configured to produce synthesis gas using endothermic plasma reforming.

25. The system of claim 15, wherein the synthesis gas generation unit is configured to use a combination of steam reformation and partial oxidation of the hydrocarbon feedstock to produce the synthesis gas.

26. The system of claim 25, wherein a ratio between steam reformation and partial oxidation used is based, at least in part, on energy available from other processes.

27. The system of claim 25, wherein the combination of steam reformation and partial oxidation achieves autothermal reforming.

28. The system of claim 25, wherein energy required to perform steam reformation is supplied by surplus electricity provided from the at least one solar or wind powered renewable energy source.

29. The system of claim 25, wherein energy released from the partial oxidation is used to perform the steam reformation.

* * * * *